(12) United States Patent
Jensen

(10) Patent No.: US 6,421,920 B1
(45) Date of Patent: Jul. 23, 2002

(54) CLAMPING AND CUTTING DEVICES

(75) Inventor: Knud Lykke Jensen, Kvistgard (DK)

(73) Assignee: Price Invena ApS, Horsholm (DK)

( * ) Notice: Subject to any disclaimer, the term of this patent is extended or adjusted under 35 U.S.C. 154(b) by 0 days.

(21) Appl. No.: 09/402,462

(22) PCT Filed: Apr. 7, 1998

(86) PCT No.: PCT/EP98/02001
§ 371 (c)(1),
(2), (4) Date: Dec. 8, 1999

(87) PCT Pub. No.: WO98/44851
PCT Pub. Date: Oct. 15, 1998

(30) Foreign Application Priority Data

Apr. 9, 1997 (GB) ................................................ 9707204

(51) Int. Cl.[7] ............................................. A61B 17/42
(52) U.S. Cl. ............................ 30/134; 30/124; 30/294; 606/120; 606/157; 606/167
(58) Field of Search .................... 30/124, 134, 131, 30/136, 280, 315, 294; 606/120, 151, 157, 158, 107, 174

(56) References Cited

U.S. PATENT DOCUMENTS

| | | | | |
|---|---|---|---|---|
| 3,323,208 A | * | 6/1967 | Hurley, Jr. ................. 30/124 X |
| 4,026,294 A | * | 5/1977 | Mattler ....................... 606/120 |
| 4,428,374 A | * | 1/1984 | Auburn ....................... 606/120 |
| 4,572,181 A | * | 2/1986 | Mattler ....................... 606/142 |
| 4,716,886 A | * | 1/1988 | Schulman et al. ............ 30/124 |
| 4,781,188 A | | 11/1988 | Collins ....................... 128/305 |
| 4,807,622 A | | 2/1989 | Ohkaka et al. ............. 128/305 |
| 4,856,517 A | | 8/1989 | Collins et al. ............. 128/346 |
| 5,127,915 A | * | 7/1992 | Mattson ....................... 606/120 |
| 5,462,555 A | | 10/1995 | Bolanos et al. ............. 606/120 |
| 5,520,699 A | | 5/1996 | Hessel et al. ............... 606/120 |
| 5,575,796 A | * | 11/1996 | King et al. .................. 606/120 |
| 5,584,840 A | | 12/1996 | Ramsey et al. ............. 606/120 |
| 5,591,173 A | * | 1/1997 | Schifano ..................... 606/120 |
| 5,676,672 A | | 10/1997 | Watson et al. ............. 606/120 |
| 5,697,938 A | * | 12/1997 | Jensen et al. .............. 30/272.1 |
| 5,797,922 A | * | 8/1998 | Hessel et al. ............... 606/120 |
| 5,817,116 A | * | 10/1998 | Takahashi et al. .......... 606/167 |
| 5,921,991 A | * | 7/1999 | Whithead et al. ........... 606/120 |
| 5,925,052 A | * | 7/1999 | Simmons ..................... 606/120 |

FOREIGN PATENT DOCUMENTS

| | | |
|---|---|---|
| WO | WO85/04091 | 9/1985 |
| WO | WO86/02541 | 5/1986 |
| WO | WO87/06449 | 11/1987 |
| WO | WO89/05125 | 6/1989 |
| WO | WO95/08953 | 4/1995 |

* cited by examiner

Primary Examiner—Boyer Ashley
(74) Attorney, Agent, or Firm—Jacobson Holman, PLLC

(57) ABSTRACT

A device for clamping and cutting an umbilical cord including a pair of differently colored clamps, each having a pair of legs joined at a hinge. A clamp holder including a cutting device supporting the clamps side by side with one another by engagement of flanged rails on the clamps in undercut slots of the clamp holder with the cutting device between them, for guiding the clamps in a sliding movement to advance the cutting desire between the clamps to cut a cord in use while compressing the legs of the clamps to clamp said cord. The clamp support disengaging from at least one of the clamps when the clamp is slid to a predetermined release point such that the clamp can be removed from the clamp holder in two directions each orthogonal to the direction of the sliding movement.

10 Claims, 6 Drawing Sheets

CLAMPING AND CUTTING DEVICES

FIELD OF THE INVENTION

The present invention relates to devices for clamping and cutting objects, e.g. for clamping and cutting an umbilical cord.

BACKGROUND OF THE INVENTION

In our earlier Patent Application WO95/08953, we described a device for squeezing and cutting members such as an umbilical cord that possesses substantial advantages in each of use, safety and ease of construction over previous devices. However, there are a number of respects in which the device described there can be still further improved.

In the device illustrated WO95/08953, when the clamp holder was lid all the way to the end of the clamps remote from their hinges, one clamp could be slid sideways out of the clamp holder by virtue of recesses in the clamp aligning with projections defining one side of the channel in which the clamp slid. When in this position, the clamp was under compression from the side walls of the channel in which it slid and the resulting friction would have to be overcome to allow the clamp to be pulled out of the channel. Also, if the clamp were moved further down the channel in this process, one or more of the said projections might get out of line with its respective projection, thus once again holding the clamp in the channel. The extraction of this clamp from the clamp holder in this way was not as rapid or easy as might be desired in an urgent situation such as the press of events that may accompany birth.

SUMMARY OF THE INVENTION

Accordingly, there is now provided according to a first aspect of the invention a clamping and cutting device comprising:

- a pair of clamps each having a pair of legs joined at a hinge at one end thereof and openable apart to receive an object to be clamped and cut,
- a clamp holder comprising cutting means and means for supporting said clamps side by side with one another with said cutting means between them and for guiding said clamps in a sliding movement within said clamp holder to advance said cutting means between said clamps to cut a said object in use whilst compressing the legs of said clamps to clamp said object,
- said clamp support means disengaging from at least one of said clamps when the clamp is slid to a predetermined release point with respect to said clamp holder such that the clamp can be removed from said clamp holder in two directions each orthogonal to the direction of said sliding movement,
- and pusher means for sliding (e.g. by pushing) said clamps through said clamp holder to said release point.

When the device is used for clamping an umbilical cord, a specific one of the two differing clamps in the illustrated device must be arranged on the baby side of the cut and the other on the mother side of the cut. One of the clamps, (the baby's clamp) is designed to come away from the clamp holder when the cord is cut and is held shut by a catch, which is not normally released.

The other (the mother's clamp) may be designed to remain in the clamp holder and is then easily released by sliding back the clamp holder along the clamp to enable sampling of the umbilical cord blood.

There may be a danger that in the heat of the moment these lamps could be put on the wrong sides of the cut. A similar problem could arise when clamping and cutting a member other than an umbilical cord which joins two dissimilar objects such that one clamp needs to be essentially permanent and the other needs to be readily openable.

This danger is greatly lessened or avoided according to a second aspect of the present invention which provides a clamping and cutting device comprising a pair of side by side dissimilar clamps and means for cutting between said clamps an object held in said clamps, said device including at least one end-obstructed finger receiving passage running transversely with respect to said side by side clamps for receiving a finger of a user gripping the device for operation thereof to carry out said clamping and cutting of said object.

Preferably said clamping and cutting device comprises said pair of clamps carried in a sliding clamp holder which slides along the clamps to force the clamps closed and carries a cutting device that passes between the clamps during said sliding of the clamp holder to cut a clamped object, and said clamp holder comprises said at least one closed-ended or end-obstructed finger receiving passage for use in gripping the clamp holder to slide the clamp holder along said clamps.

In an alternative approach to relieving the same problem, optionally usable in conjunction with said first or said second aspect of the invention, there is provided according to a third aspect a clamping and cutting device comprising a pair of structurally dissimilar clamps and means for cutting between said clamps an object held in said clamps, wherein the clamps are differently coloured.

In the device of WO95/08953, the two clamps had flat bodies. The one clamp had its longitudinally running edges received in opposed slots in the clamp holder, and when the clamp holder was fully at the hinge end of the clamp, there was little to prevent it from coming off the hinged end of this clamp. The hinge of the clamp was an enlarged diameter, part circular region of the clamp, but this would not provide sufficient retention of the clamp in the holder to enable it to be inserted upon manufacture and to remain in place reliably until use. Rather, it was expected that the clamp would be assembled to the clamp holder immediately before use. The other clamp ran in a channel defined on one face of the clamp by the web of the clamp holder and on the other by spaced nose-like projections, allowing for the clamp to be released when locked closed. Once again, this arrangement would not be sufficient to allow factory assembly. It has now been appreciated that is it advantageous for the clamps to be sufficiently reliably held in the clamp holder prior to use that the entire device can be assembled for use well in advance, e.g. at manufacture, without significant risk that either clamp will come out of the holder until the clamp holder has been used.

To improve the reliability with which the clamps are held in the clamp holder prior to use the invention provides according to a fourth aspect of the invention a clamping and cutting device comprising a pair of clamps each having a pair of legs hinged together at one end and openable apart to form an opening to receive an object between them to be clamped and cut, a clamp holder provided with a pair of clamp receiving channels defined between opposed wall members and separated by a web member connecting said wall members, which web member carries a cutting means, whereby the clamp holder can be slid along said clamps from the hinged end thereof to said other and to force said clamps shut and cut an object clamped therein, wherein each said channel and the respective clamp received therein are connected for relative sliding movement by the provision of a flanged rail on one of them received in and sliding in an undercut slot on the other.

Preferably an abutment is provided obstructing removal of one of the said clamps by sliding movement thereof out of said clamp holder.

All of the different aspect of the invention, or any desired combination of them may be used in combination as will be illustrated hereafter by the description of a preferred embodiment in which they are all combined.

BRIEF DESCRIPTION OF THE DRAWINGS

This device is illustrated in the accompanying drawings in which.

DETAILED DESCRIPTION OF THE PREFERRED EMBODIMENTS

The device according to the illustrated embodiment comprises three main components namely a clamp holder, which incorporates a cutting device, and two dissimilar clamps.

Figure 1:
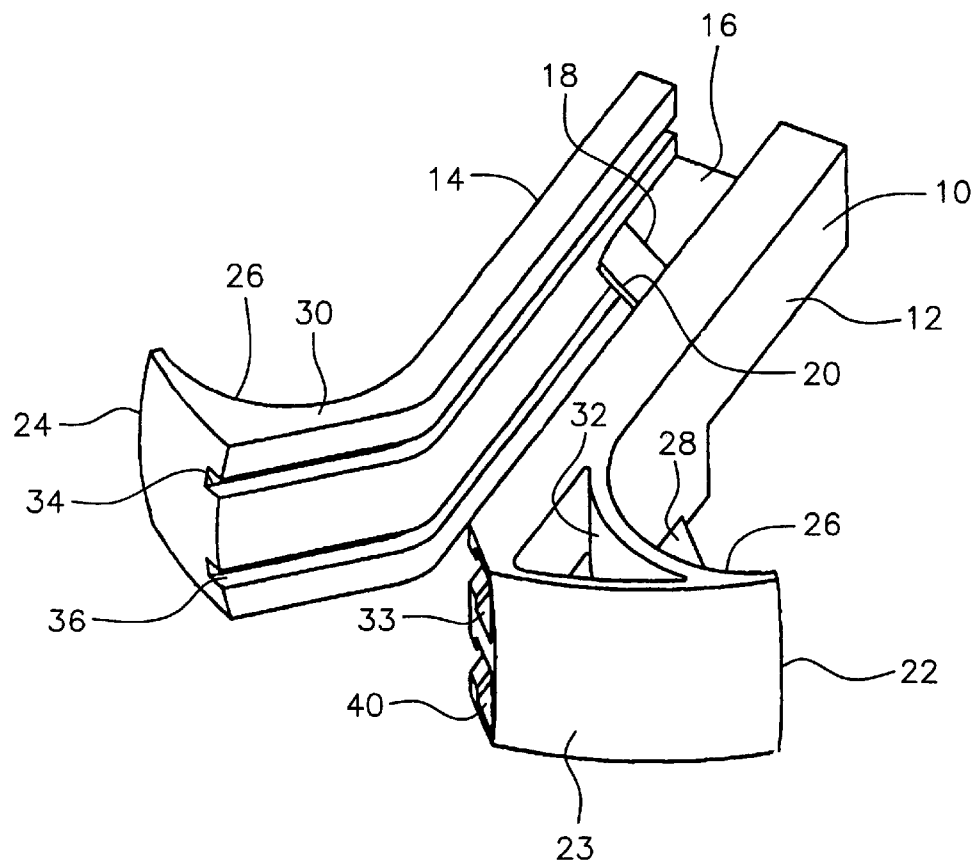
FIG. 1 is a perspective view from the front of the clamp holder of the embodiment.
Figure 2:
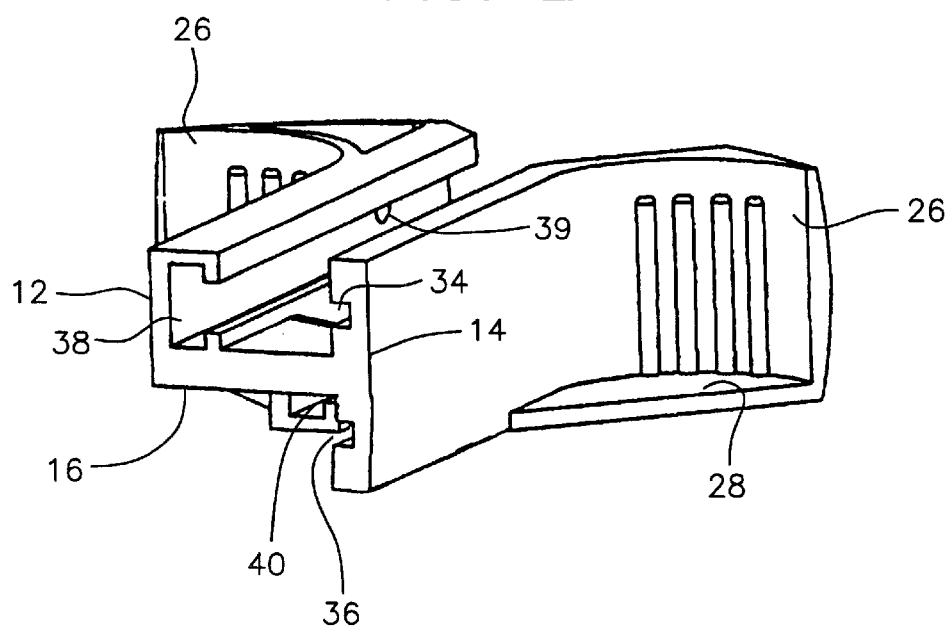
FIG. 2 is a perspective view from the rear of the clamp holder of FIG. 1.

As shown in FIG. 1, the clamp holder 10 comprise a first wall member 12 and a second wall member 14. In a rear portion of the holder, the wall members 12 and 14 extend in parallel spaced relationship and are connected by a web 16 which extends forward from the rear end of the device along approximately half the length of the parallel portions of the wall members 12 and 14. At its forward end, the web 16 slopes from the wall member 12 rearwardly to its connection to the wall member 14 as a forward edge 18. Within the thickness of the web there is set a metal knife blade 20 whose cutting edge slopes parallel to the forward edge 18 of the web.

From just forward of the most forward point of the knife blade 20 back to the rear of the clamp holder 10, the wall member 12 has a cut away portion such that all of the wall member to one side of the web is omitted. Optionally, the wall member 14 may be similarly cut away in the region opposite to the cut away in the wall member 12.

At the forward ends of the wall members 12 and 14, there are provided a pair of finger engagement wings 22, 24 integrally moulded with the wall members 12, 14 and extending laterally cut therefrom. These include a concave finger engaging surface 26 defining a finger receiving passageway extending from the upper surface of the clamp holder as shown in FIG. 1 downwards to an end plate 28 in each case. The end plate 28 serves to close the finger receiving passageway defined by the surface 26 on each wing. Wall member 14 has an outwardly diverging portion 30 at its forward end whilst wall member 12 extends in a straight line to the front of the device. The front of wing 22 is formed as a convex surface 23 and the space between the convex surface 23 and concave face 26 embraces an approximately triangular cross-section hollow 32 to save material and to control shrinkage.

Above and below the web 16, the wall members 12, 14 together with the web 16 define a pair of channels. Each channel is for receiving a respective clamp as described hereafter. To guide movement of the clamps, each channel is provided with guide slots. In wall member 14, there are provided guide slots 34 and 36, each of which is a plain rectangular slot extending from the rear end of wall member 14 to its front end, including the outwardly diverging or flaring portions 30.

In wall member 12, each slot 38, 40 is undercut in a T-shape. The surface of wall member 12 forming the top of the head of the "T" of the slot 38 has a dog 39 providing a rear facing abutment surface.

Figure 3:
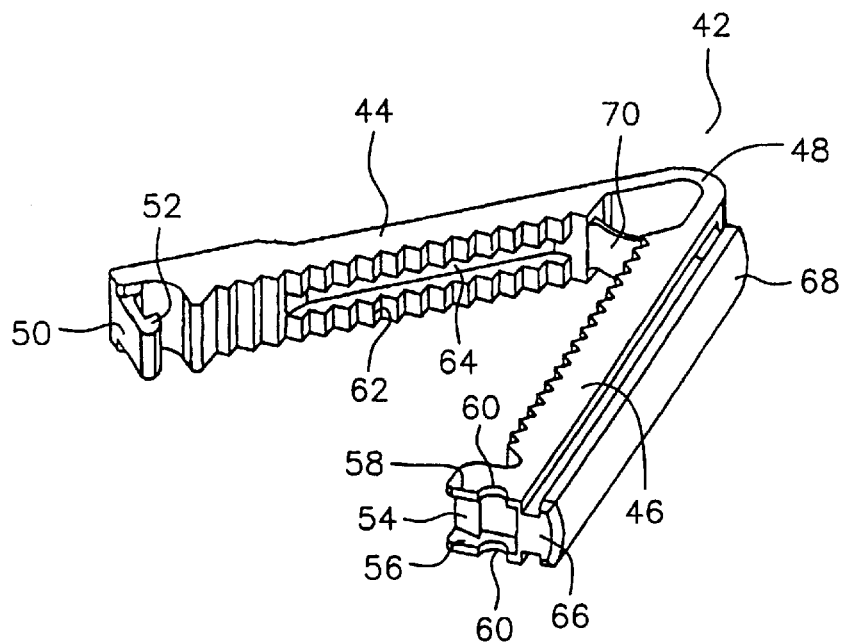
FIG. 3 is a perspective view of a first clamp of the embodiment.

A first clamp for the device is shown in FIG. 3. This clamp is intended to clamp an umbilical cord on the baby's side. The clamp 42 comprises a pair of legs 44, 46 joined at a resilient integrally moulded hinge 48 by which the legs are sprung apart. At their free ends, the legs are provided with a catch mechanism comprising a catch 50 extending inwardly from leg 44 and having a hooked end 52 which co-operates with an outwardly facing abutment surface on a dog 54 provided at the free end of leg 46. Dog 54 is provided at the base of a channel extending across the end of leg 46 and defined by forwardly protruding channel walls 56, 58 in each of which is provided a forwardly facing arcuate depression 60.

The interior surface of each leg 44, 46 is provided with a row of transversely extending teeth 62 for gripping a cord when the clamp is shut. Running longitudinally of each leg central within the width of the teeth 62 is an open slot 64 which assists in preventing movement of the clamp along the length of the cord in use.

Leg 46 is provided on its exterior surface with a rail 66 bearing a flange 68 producing a T-shape, matching slot 40 of the clamp holder in which it is adapted to be received. On the exterior of the other leg (not shown) there is provided a rail to engage in slot 34 of the clamp holder.

Finally, the clamp 42 has extending from leg 46 a flexible shield 70 for preventing the cord in use passing into the hinge 48 and escaping from the teeth of the clamp.

Figure 4:
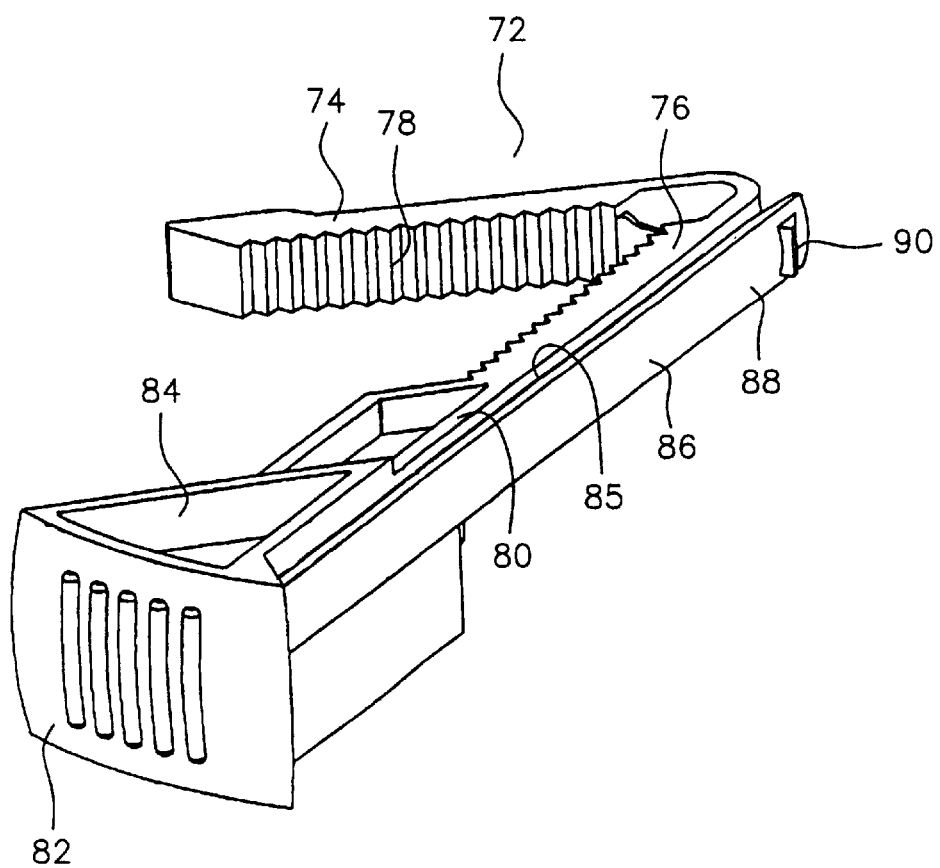
FIG. 4 is a perspective view from the front of a second clamp of the embodiment.
Figure 5:
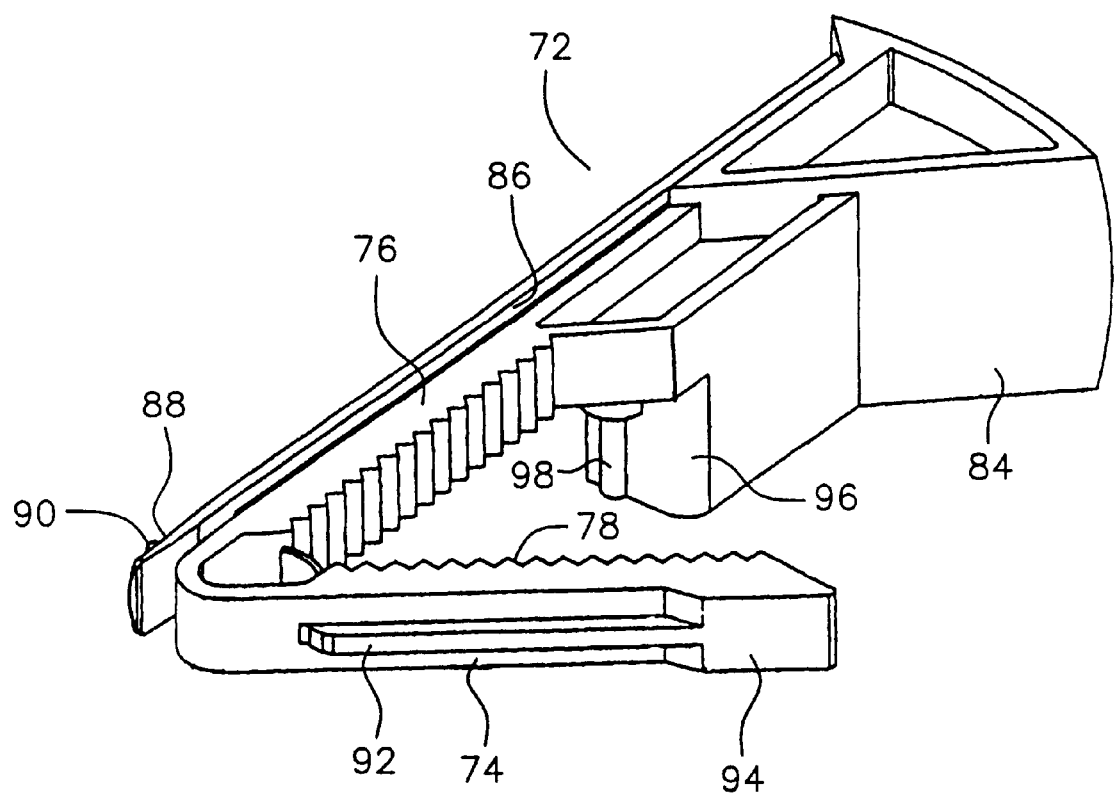
FIG. 5 is a perspective view from the rear of the clamp of FIG. 4.
Figure 6:
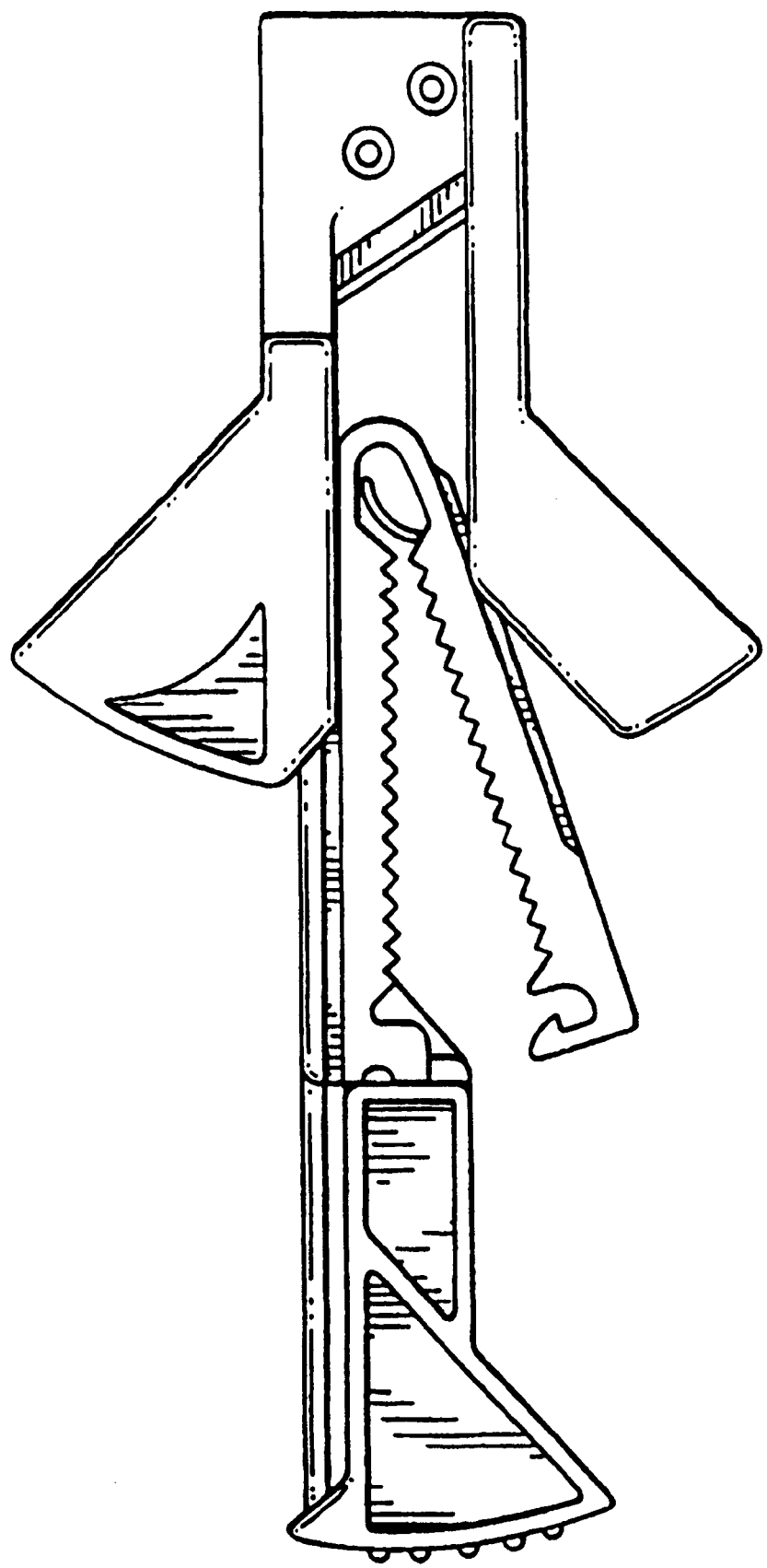
FIG. 6 is a plan view from one face of the device of FIGS. 1 to 5 assembled ready for use.
Figure 7:
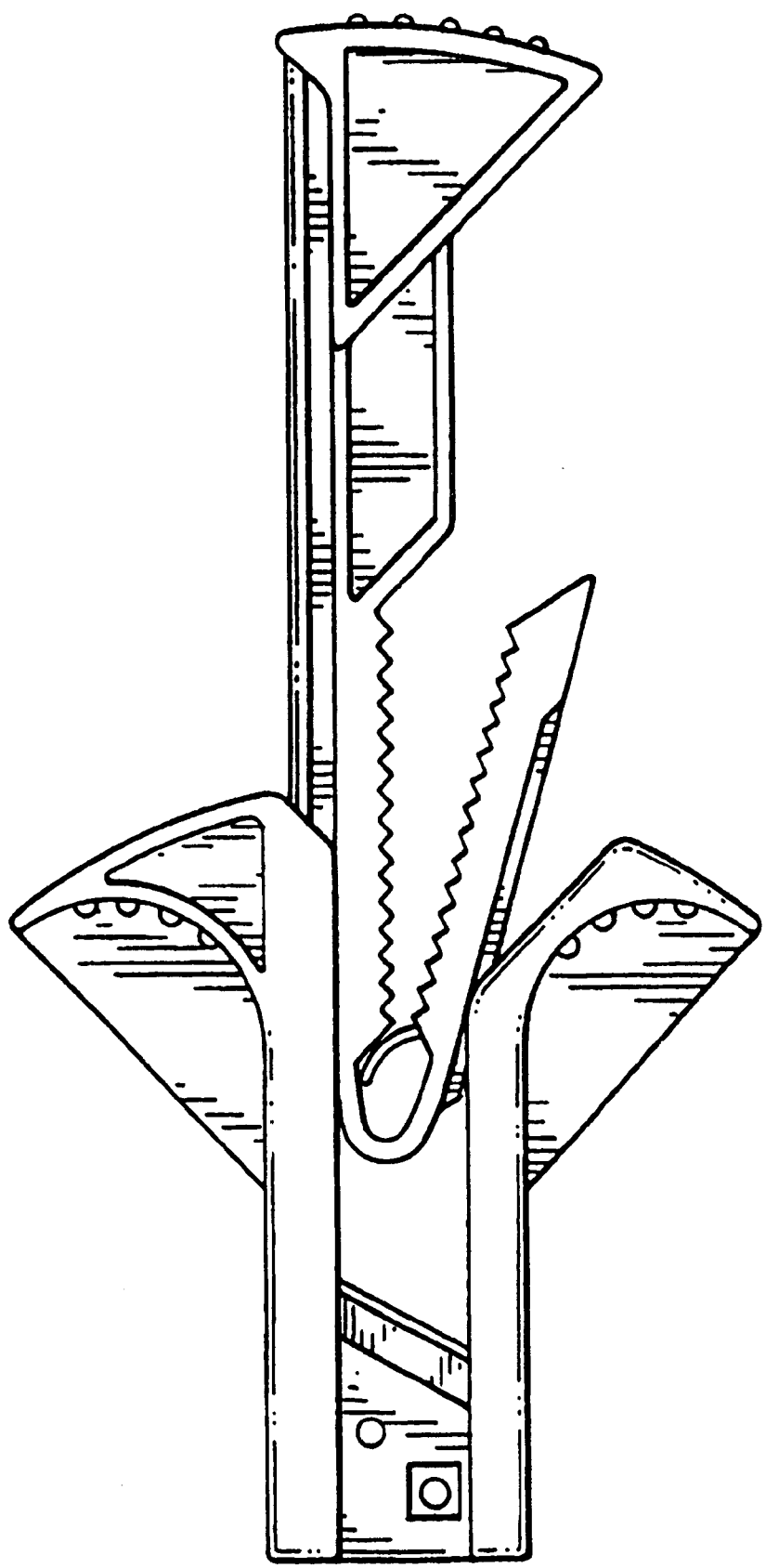
FIG. 7 is a plan view of the opposite face of the device of FIGS. 1 to 6 assembled ready for use.

The second clamp 72 is shown in FIG. 4 and comprises a first leg 74 and a second leg 76 which are joined by a resilient hinge and outwardly sprung in the same manner as described in connection with the first clamp. Like the first clamp, each leg has a row of teeth 78 extending transversely of the leg.

The leg 76 of the clamp 72 is extended in its forward direction to form a pusher 80 having at its forward end a thumb engaging surface 82 formed on an enlarged head portion 84. Along the outside of leg 76 there is provided a T-shaped rail 85 incorporating a flange 86 similar to that on the first clamp and adapted to be received in T-shaped slot 38 of the clamp holder. The flange 86 is extended rearwardly beyond the end of the rail to form a resilient rail 88 bearing a tooth 90 having a forwardly facing abutment surface which is adapted to engage behind the rearward facing abutment surface of the dog 39 of the slot 38.

Leg 74 has on its outer surface a rail 92 similar to the corresponding rail (not shown) on the first clamp. Rail 92 runs in slot 34 of the clamp holder. Rail 92 terminates short of the forward end of leg 74 and in this region leg 74 has an enlarged head 94. A similar arrangement is present at the head end of leg 44 of clamp 42.

Adjacent the end of leg 76, the pusher head 84 has a rearwardly facing abutment surface 96 with a rearwardly projecting arcuate nose 98.

For use, the device is assembled by passing the rearward end of the T-shaped rail 86 into the forward end of the T-shaped slot 38 of the clamp holder until the tooth 90 passes the dog 39, thus retaining the clamp 72 in the clamp holder. The clamp 42 is assembled into the clamp holder by passing the tail end of the T-shaped rail 66 into the mouth of the slot 40 of the clamp holder. The device is then ready for use. Both clamps are open. The device may be packaged in this form and may be supplied ready for use from the factory in which it is made.

Figure 8:
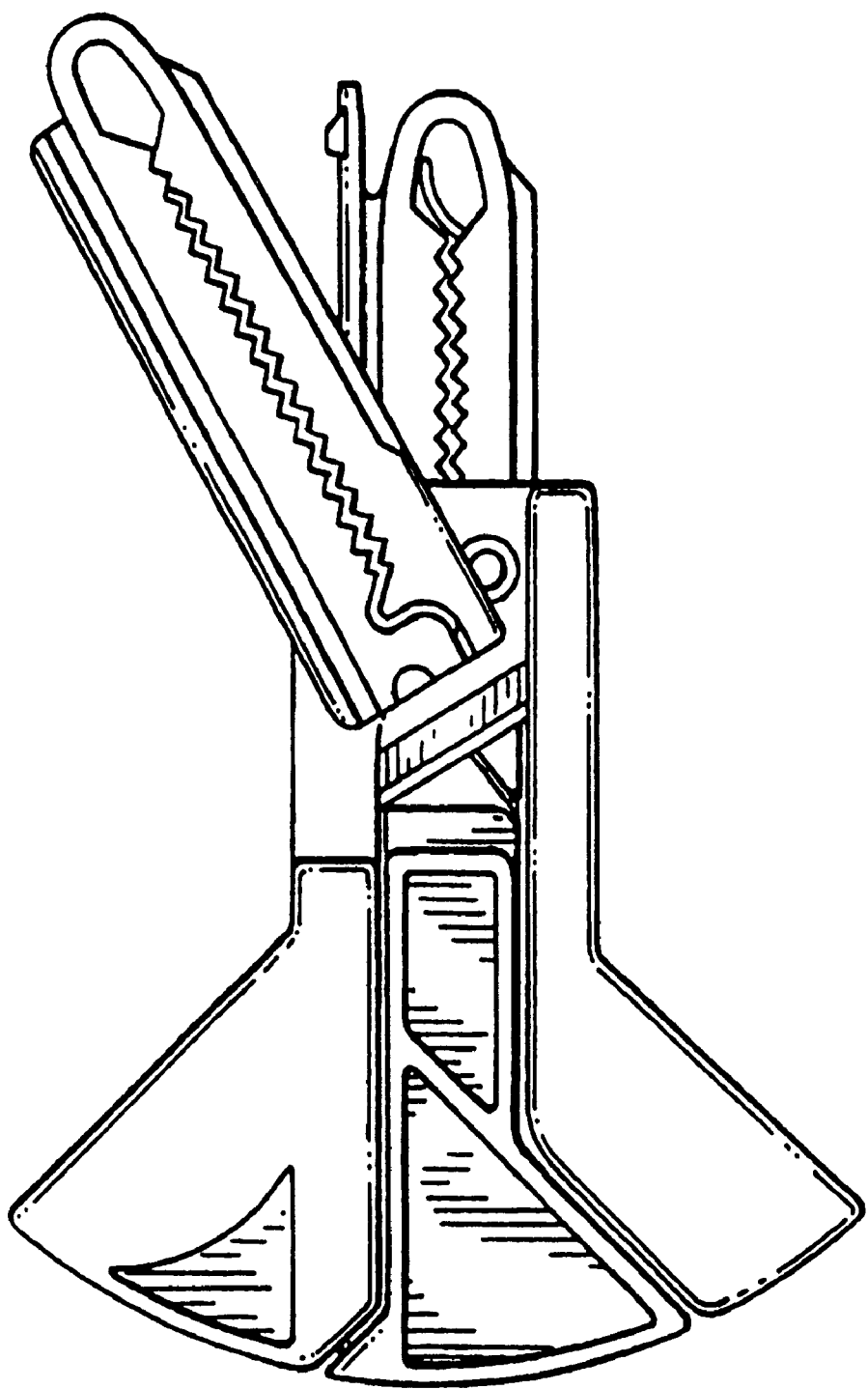
FIG. 8 is a plan view of the device of FIGS. 6 and 7 as it appears immediately after use.

In use to cut an umbilical cord, the operator grips the device by placing the operator's thumb against surface 82 and placing the first and second fingers into the finger receiving passageways defined by the arcuate surfaces 26 until they abut against the plates 28 of the clamp holder. The smooth underside of the clamp holder is then placed against the surface of the stomach of a baby during delivery so that the umbilical cord falls into the open mouths of the clamps 42 and 72. By then pressing the pusher head 84 at the head of the clamp 72 with the thumb as if operating a syringe, the clamps are driven to slide synchronously through the clamp holder. The pushing action is conveyed to the clamp 42 by the engagement of the nose 98 in the recesses 60. As the clamp 42 comes into the parallel walled portion of its channel in the clamp holder, the catch 50 is driven between the projecting walls 56, 58 to become closed and engaged. When the head end of the clamp 42 reaches the rear end of its T-shaped slot 40, as shown in FIG. 8, the clamp 42 is ejected from its channel in th clamp holder and is free to move away both upwardly out of the plane of the drawing in FIG. 8 and laterally away from the wall member 14.

The clamp 42 may be made from a different coloured material from the rest of the device. Suitably, all of the components except the cutting blade may be moulded in plastics such as nylon 66.

Many modifications and variations of the invention as described with reference to the specific embodiment may be made within the scope of the invention. For instance, instead of one clamp remaining captive in the clamp holder, both clamps may be made to eject from the clamp holder in a similar way on being pushed fully home. The pusher may be provided with its guide slot in the clamp holder and may push against each clamp in the same way that it pushes against clamp 42 in the illustrated embodiment.

I claim:

1. A clamping and cutting device:
   a pair of clamps each having a pair of legs joined at a hinge at one end of said legs and said legs being openable apart to receive an object to be clamped and cut,
   a clamp holder comprising cutting means and means for supporting said clamps side by side with one another with said cutting means between them and for guiding said clamps in a sliding movement within said clamp holder to advance said cutting means between said clamps to cut said object in use whilst compressing the legs of said clamps to clamp said object,
   said means for supporting said clamps disengaging from at least one of said clamps when the clamps is slid to a predetermined release point with respect to said clamp holder such that the clamp is removable from said clamp holder in two directions each orthogonal to the direction of said sliding movement,
   and a mutually engageable surface on said clamp for sliding said clamps through said clamp holder to said release point.

2. A clamping and cutting device as claimed in claim 1, wherein said clamp holder comprises at least one end-obstructed finger receiving passage running transversely with respect to said side by side clamps for receiving a finger of a user gripping the device for operation thereof to carry out said clamping and cutting of said object.

3. A clamping and cutting device as claimed in claim 1, wherein said one clamp and said other clamp are one of differently coloured and differently visually patterned.

4. A clamping and cutting device as claimed in claim 1, wherein said clamp holder is provided with a pair of clamp receiving channels each receiving one of said pair of clamps, said channels are defined between opposed wall members and separated by a web member connecting said wall members, said web member carrying said cutting means.

5. A clamping and cutting device as claimed in claim 4, wherein the channel for one of said clamps is of such a length that when the clamp is slid to said release point said clamp is expelled from said channel in which the clamp is received.

6. A clamping and cutting device as claimed in claim 5, wherein the channel for the other of said clamps is of such a length that when the clamps are slid to being said one clamp to the release point said other clamp is still retained in said channel is which the clamp is received.

7. A clamping and cutting device as claimed in claim 4, wherein each said channel and a respective clamp received therein are connected for relative sliding movement by a flanged rail on one of them received in and sliding in an undercut slot on the other of them.

8. A clamping and cutting device as claimed in claim 7, wherein an abutment is provided obstructing removal of said other clamp by sliding movement thereof out of said clamp holder.

9. A clamping and cutting device comprising a pair of clamps each having a pair of legs hinged together at one end and being openable apart to form an opening to receive an object between them to be clamped and cut, a clamp holder provided with a pair of clamp receiving channels defined between opposed wall members and separated by a web member connecting said wall members, said web member carrying a cutting means, whereby, in use, the clamp holder is slid along said clamps from the hinged end thereof to said other end to force said clamps shut and cut an object clamped therein, wherein each said channel and a respective one of said pair of clamps received therein are connected for relative sliding movement by the provision of a flanged rail on one of them received in and sliding in an undercut slot on the other.

10. A clamping and cutting device as claimed in claim 9, wherein an abutment is provided obstructing removal of one of said clamps by sliding movement thereof out of said clamp holder.

* * * * *